United States Patent [19]
John

[11] Patent Number: 4,846,190
[45] Date of Patent: Jul. 11, 1989

[54] ELECTROENCEPHALOGRAPHIC SYSTEM DATA DISPLAY

[76] Inventor: Erwin R. John, 930 Greacen La., Mamaroneck, N.Y. 10543

[21] Appl. No.: 44,438

[22] Filed: Apr. 30, 1987

Related U.S. Application Data

[63] Continuation-in-part of Ser. No. 842,498, Mar. 21, 1986, abandoned, which is a continuation of Ser. No. 525,628, Aug. 23, 1983, Pat. No. 4,557,270.

[51] Int. Cl.$^4$ ............................................... A61B 5/04
[52] U.S. Cl. ................................................... 128/731
[58] Field of Search ......................... 128/731, 732, 733

[56] References Cited

U.S. PATENT DOCUMENTS

| | | | |
|---|---|---|---|
| 4,407,299 | 10/1983 | Culver | 128/732 |
| 4,417,591 | 11/1983 | Culver | 128/731 |
| 4,421,121 | 12/1983 | Whisler et al. | 128/731 |
| 4,579,125 | 4/1986 | Strobl et al. | 128/731 |
| 4,592,369 | 6/1986 | Davis et al. | 128/733 |

Primary Examiner—Francis Jaworski
Assistant Examiner—George Manuel
Attorney, Agent, or Firm—Eliot S. Gerber

[57] ABSTRACT

An EEG (electroencephalograph) system detects a patient's brain waves from electrodes pressed against the patient's scalp, amplifies the analog brain waves and converts them into digital signals. The digital brain waves are processed to reduce electrical interference, muscle artifact and other noise, and then compared on a statistical basis against the patient's self-norm and population norms derived from groups of normal and abnormal groups of patients under specified conditions. The results of the statistical analysis, on an almost real-time basis, are displayed on a CRT color monitor. Two alternative embodiments of displays are:

(1) Sequential analyses of time segments, intensity modulated to reflect statistical significance, are displayed in eight areas corresponding to eight brain sectors using a moving window type of histogram, stacked from top to bottom in temporal sequence;

(2) Lights are laid out on a control console in the form of a topographic head map and the color of the lights is coded to correspond with the results of statistical analysis.

20 Claims, 7 Drawing Sheets

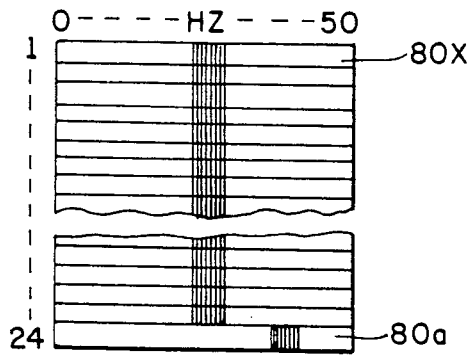
FIG. 4
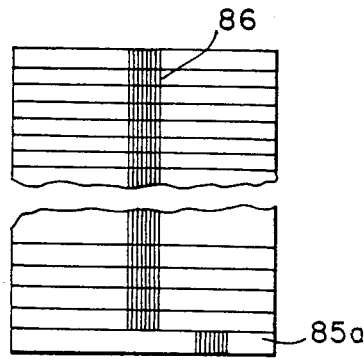
FIG. 5
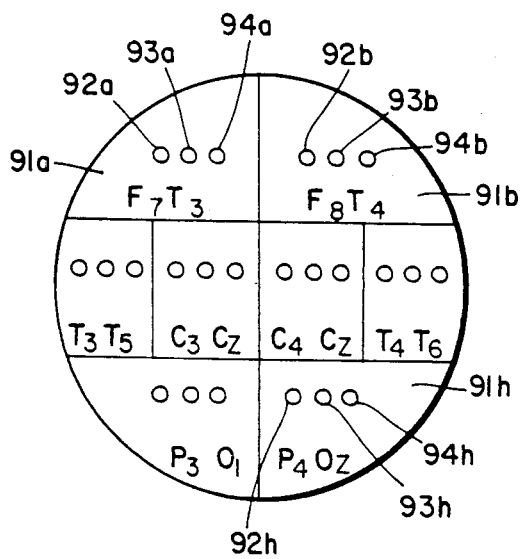
FIG. 6
FIG. 7
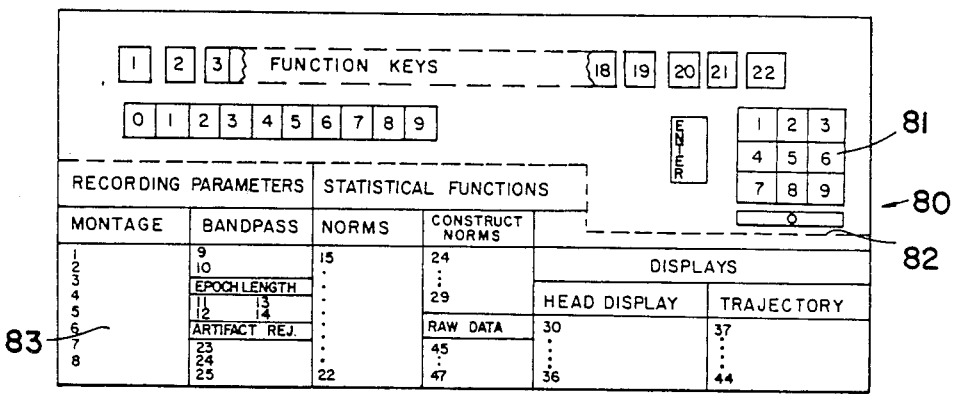

ELECTROENCEPHALOGRAPHIC SYSTEM DATA DISPLAY

BACKGROUND OF THE INVENTION

This application is a continuation-in-part based, in part, upon the inventor's prior copending application Ser. No. 06/842,498, filed Mar. 21, 1986 and entitled "Electroencephalographic System For Intra-Operative Open-Heart Surgery," abandoned, which was a continuation of application Ser. No. 525,628, filed Aug. 23, 1983, now U.S. Pat. No. 4,557,270, issued Dec. 10, 1985.

The present invention relates to medical apparatus and more particularly to the display in an EEG (electroencephalograph) system.

Generally, in conventional EEG systems, a group of electrodes, for example 19 electrodes, are connected to the scalp of the patient. The electrodes, using conductive paste, are in electrical contact with the scalp and detect the patient's electrical brain waves which are analog signals. The analog brain wave signals are amplified and recorded by a multi-pen recorder. In clinical neurophysiology, a clinician uses subjective impressions or visual pattern recognition of EEG and EP (evoked potential) recordings to recognize abnormal morphologies, i.e., unusual patterns. The normal or reference pattern is provided by a mental image in the mind of the clinician. The validity of the results depends upon the training, skill and attention of the clinician.

A series of prior patents, including the inventor's U.S. Pat. Nos. 4,557,270 (incorporated by reference herein); 4,279,258; 4,201,224; 4,188,956 and 4,171,696, have suggested that the analog brain waves be converted to sets of digital data which are analyzed on a statistical basis and the statistical results displayed on a CRT or printed out by a computer printer. Such computer based statistical analysis provides an objective view of certain quantitative features extracted from EEG and EP recordings.

A major difficulty, however, has been the problem of presenting the mass of digital data in a useable form. If the data are simply printed out, in numbers, the mass of information is so great as to be almost useless. For example, a typical patient examination may produce over 2,000 meaningful numbers.

A number of patents suggest that the presentation of the data, instead of a print-out of numbers, should be in the form of a topographic map in which each portion of the display corresponds to an electrode or a head sector. For example, the inventor's prior U.S. Pat. No. 4,188,956, at FIGS. 2 and 3, shows such a topographic patient head map. That patent discloses the formation of matrices whose cells are the results of statistical analysis of quantitative features of the patient's brain waves in different anatomical regions. The matrices are displayed as topographic maps of the head, with the statistical evaluation of each brain region being displayed in the corresponding sectors of the map of the head using colored lights, with the color indicating normality or the degree of abnormality. Interpolated colored topographic maps, representing the brain, in which graded values of potential or of abnormality in pixels between electrodes are calculated by interpolation and are represented by different colors, are disclosed in Duffy U.S. Pat. Nos. 4,408,616 and 4,421,122; and Culver 4,407,299 and 4,417,591.

One type of color-coded topographic representation presents the EP as a "map-movie"; a series of maps showing the interpolated spatial distribution of potentials (at different times) along an analysis epoch, with different colors representing different potential values.

Interpolated topographic maps of the EEG are vulnerable to criticism because they are extremely redundant, in that thousands of hypothetical pixel values are calculated at positions intermediate to the locations of a small number of electrodes where actual voltages are measured. They can be misleading, because true maxima or minima between electrodes may not be detected. Color coded actual voltage values can present a bewildering kaleidoscopic phenomenology difficult for the clinician to interpret. Color coded statistical evaluations of individual deviations from norms are easier to interpret, but depend critically upon the appropriateness of the reference normative data and the adequacy of the statistical procedures.

Interpretability is further made difficult by the fact that topographic EEG maps are usually derived from a brief sample of EEG assumed to be typical, with no way to estimate the reliability of that sample as a reflection of the current state of the brain nor to evaluate the sample as a time point in the context of a short term or long term trend, during which the state may fluctuate or change systematically. Evoked potential (EP) map movies suffer further from the high degree of intercorrelation between values at the same topographic location across successive "frames", i.e., time points in the analysis epoch. This redundancy in time as well as space makes EP topographic movies particularly difficult to evaluate, and diagnostic features can readily be misperceived or overlooked.

Finally, a potentially invaluable source of information about relationships among various brain regions is available from quantifications of the amount of "phase-locked" or synchronized EEG activity between pairs of electrodes, as reflected in the cross-spectral coherence matrix for each frequency band of the EEG between each electrode and every other electrode. The topographical representation of the full set of coherent activities across the head, in a comprehensible and statistically interpretable manner, can provide a powerful tool for visualizing subtle changes in transactions between brain regions, and has hitherto not been available. The analytic methods and graphic displays embodied in the invention are intended to resolve these various shortcomings and inadequacies of current EEG and EP mapping methods.

The description of the invention which follows is in terms of an EEG apparatus to monitor cardiovascular surgical operations on an on-line basis to indicate to the surgeon whether measures should be taken, such as changing the blood flow or pressure from the cardiopulmonary bypass apparatus, to prevent brain damage. However, the present invention is applicable to many other types of EEG and EP uses, including the monitoring of other surgical procedures, the monitoring of anesthesia, the examination of patients with neurological or psychiatric disorders, the mass screening of subjects for brain dysfunctions, and the evaluation of changes in brain functional relationships correlated with mental activity or interactions between a subject and a psychiatrist or other medical examiner.

OBJECTIVES AND FEATURES OF THE INVENTION

It is an objective of the present invention to provide a display in an EEG system which will present the results of statistical analysis of a subject's brain waves in a form which is readily comprehended.

It is a further objective of the present invention to present such a display which operates on an almost real-time basis so that the data may immediately be acted upon and remedial action taken.

It is a further objective of the present invention to present such a display which will quantify the functional state of the different head sectors relative to a selected reference state so that any abnormalities may be connected with specific head sectors, and the extent of abnormality or changes in each sector may be viewed and readily comprehended.

It is a further objective of the present invention to present information about the distribution of power in frequency bands of the EEG spectrum in different brain regions by representing the spectrum as a line and by coding the power at any frequency by the color of the corresponding line segment in a topographic display. Power spectral analyses of successive EEG samples can then be represented by closely packed vertical stacks of horizontal lines in chronological sequence in each region of the topographic map, which will be called a Color Coded Topographic Spectral Array, or CCTSA.

It is a feature of the present invention that a simplified and readily comprehended visual display be presented to the clinician or surgical personnel which describes the patient's on-going brain activity. The first embodiment of the display presents, as to each of eight bipolar or nineteen monopolar brain sectors, a moving window type of histograph. A self-normed reference or "baseline" set of brain wave data is comprised of a group of time segments for each derivation, for example, 24 segments, which are collected, analyzed, displayed and statistically compared, as a group, with the next occurring time segment of brain wave data, as well as with population normative data or with the data from patients with normal outcome under similar flow and temperature conditions. As data are collected, the oldest segment is removed from the group and the latest segment added, and the window scrolls upwards The EEG data is processed so that segments containing muscle artifact, and other noise, are automatically detected and are excluded from these comparisons. The statistical evaluation relating to the selected reference data and the color-coded visual display provide an immediate and apparent indication as to whether the current brain wave segments in any derivation are significantly different from the patient's own on-going prior set of brain wave EEG segments or from the normative data observed in the patient in some prior reference state, in the "normal outcome" group under the same conditions, or in some other reference group.

It is a still further feature of the invention that, in a second and alternative embodiment having a simplified visual display, a set of color coded lights are used on a panel having a head outline divided into sectors corresponding to recording derivations. The same statistical data processing occurs for each electrode or derivation, comparing a moving group of 24 segments with the next segment and then with the next group of segments, as well as with any prior baseline, population norms, or the normal outcome data. For example, for each head sector the light is green when the comparison shows no meaningful change; the light is amber when the next segment is significantly different at the $p \leq 0.05$ level from the current group, population norma, self-norm, or normal outcome data; and the light is red when the new group is significantly different at the $p \leq 0.01$ level from the prior group, population norms, self-norm, or normal outcome data.

It is a still further feature of the invention to provide a third alternative visual display embodiment. In this third alternative embodiment a topographical map is displayed in which blocks, arranged in columns and rows on a CRT monitor, correspond to sectors on the patient's head. Each of the blocks of this embodiment consists of a matrix of rows and columns of colored line segments, dots or squares, for example, four to forty rows and six columns. The bottom row represents the analysis of the most recent sample and the rows are scrolled upwards. Each column represents an analysis of a different variable or "feature"; for example, each column may represent a separate frequency band. The frame around the block representing a sector will flash to provide a warning of significant changes within any feature or across any set of features, taking their intercorrelation into account, using the "mahalanobis distance" based upon their covariance matrix. The blocks are connected by color coded horizontal and vertical lines, in different respective "levels", i.e., pictures of different features such as coherence or symmetry, which may be superimposed or viewed alone. Occurrence of a significant change in any feature not currently displayed is detected by assessing the total feature set and, in the event that the critical feature is not displayed, presenting a message informing the user of the site of meaningful change.

In a fourth alternative display, a topographic map of the head is displayed on a video (TV) color monitor. Each head sector is represented by a "tile" (block) which is color coded to reflect the significance of deviation from the current reference. This may be considered a simplified version of the third embodiment which omits the cross-correlations and symmetries shown by the horizontal and vertical lines.

In the fifth alternative display, a large number of separate topographic maps of the head are displayed simultaneously on a video (TV) color monitor. For example, 19 "heads" may be displayed. Each head display preferably has 19 map areas ("tiles") corresponding to 19 head areas each having an electrode attached thereto, according to the international 10/20 system, for example. Each of the 19 tiles displays the normed cross-correlation of one electrode, i.e., one head area, with each of the other 18 color coded for statistical significance. At one time and on one screen the operator may view, in a readily comprehended manner, the $19 \times 19$ or 361 cross-correlations in one frequency band. The screen display is readily changed to provide the same type of display at each set of measures, for example, at each of four frequency bands, i.e., delta, theta, alpha, beta and the multivariate composite or mahalanobis distance across the four bands, taking their intercorrelations into account. Alternatively, the cross-spectral coherence can be simultaneously displayed for five heads, one for each of the four frequency bands and one for the composite, showing $5 \times 361$ or 1805 relationships.

BRIEF DESCRIPTION OF THE DRAWINGS

Other objectives and features of the present invention will be apparent from the following detailed description which should be taken in conjunction with the accompanying drawings.

In the drawings:

FIG. 4 is a front plan view illustrating one of the color-coded topographic spectral arrays (CCTSA) of the first embodiment of the displays of the present invention, for one derivation, under a first set of conditions;

FIG. 5 is a front plan view illustrating a similar CCTSA, as in FIG. 4, under a different set of conditions;

FIG. 6 is an illustration of a portion of the display panel showing the second alternative embodiment of the display;

FIG. 7 is an illustration of an additional control panel which may be used in connection with the control and display panel of FIG. 3;

DETAILED DESCRIPTION OF THE INVENTION

Figure 1:
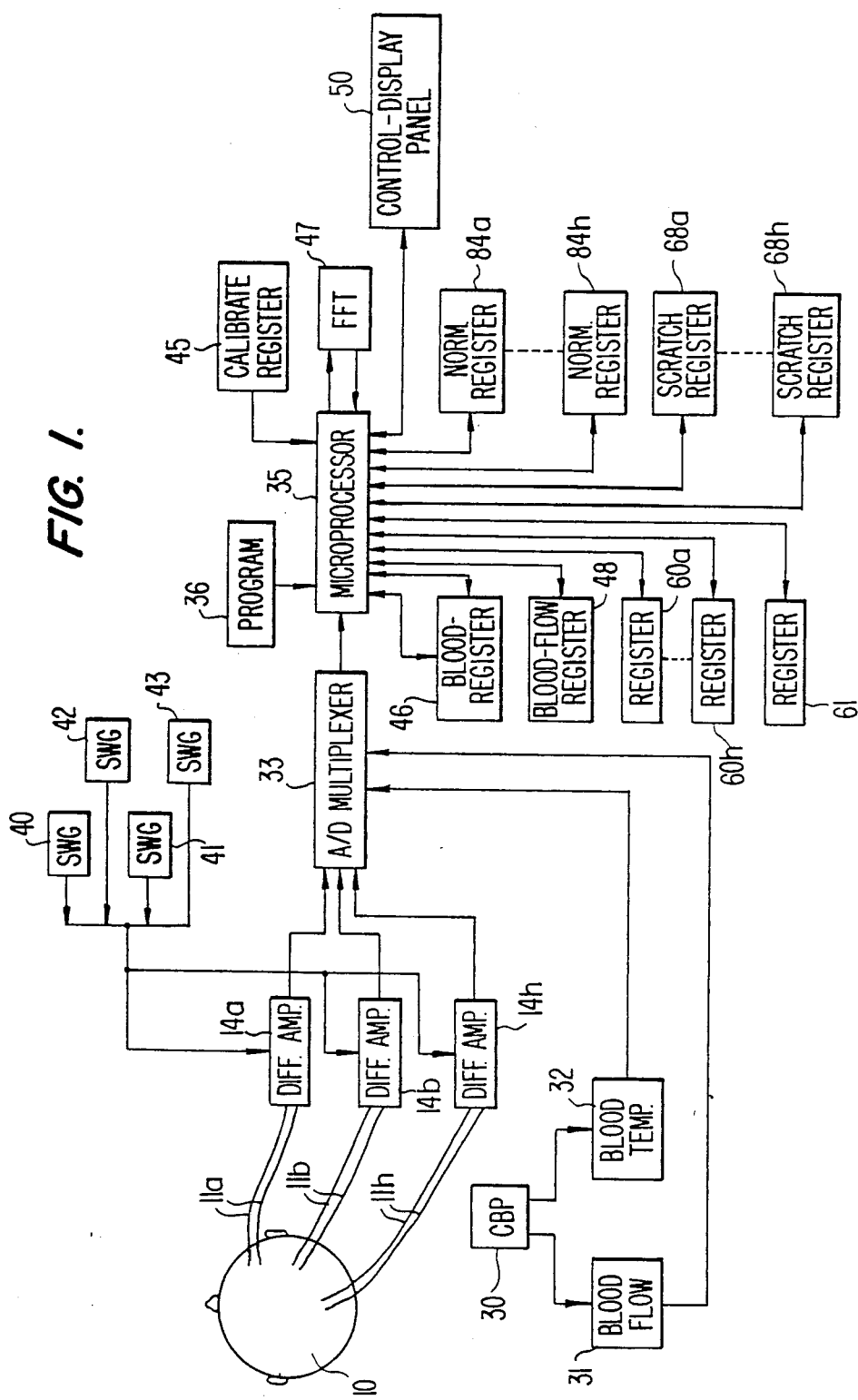
FIG. 1 is a block schematic diagram of an EEG system which may be used with the displays of the present invention.
Figure 2:
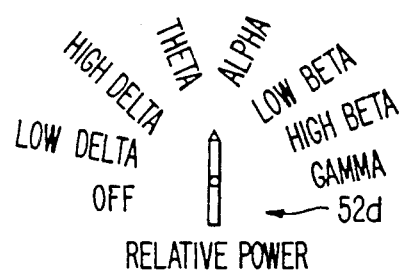
FIG. 2 is a front plan view of a portion of the control panel of FIG. 3.

The apparatus of the present invention is described in connection with the block diagram of FIG. 1 showing the various components of the system. The brain function of the patient who is to be operated upon should be evaluated before the operation (or procedures) during the operation, and after the operation. Essentially the same apparatus may be used at all three times with, however, proper modifications for use before and after the operation or procedure.

The system of FIG. 1 will be described primarily in connection with its use during the surgical operation. It will be described, in certain places, in terms of a coronary artery bypass surgical procedure. However, it will be understood that other cardiac or vascular surgical procedures, or even general surgery, will benefit from using the apparatus of the present invention. The displays of the present invention are adapted for general EEG use, including monitoring of anesthesia, examination of patients with neurological or psychiatric disorders, etc.

As shown in FIG. 1, the head 10 of the patient is connected to a set of electrodes. The conventional 19-electrode International 10/20 electrode placement system and nomenclature is preferably used. Only three pairs of electrodes 11a, 11b, and 11h are shown in FIG. 1 so as to simplify the drawing. However, preferably 19 electrodes are used to provide 19 monopolar or 8 bipolar (constructed or direct) derivations. The preferred bipolar derivations would be $F_7 T_3$, $F_8 T_4$, $T_3 T_5$, $T_4 T_6$, $C_3 C_z$, $C_4 C_z$, $P_3 O_1$ and $P_4 O_2$. However, other bipolar derivations might be constructed. Further information regarding the computed construction of pair derivations may be obtained from the invention's prior patent entitled "System And Method For Electrode Pair Derivations in Electroencephalography", Ser. No. 873,118, U.S. Pat. No. 4,411,273, incorporated by reference herein. Differential amplifiers can also be used for bipolar derivations.

As few as 8 and as many as 19 amplifiers might be used to implement this system. Most of the examples given herein illustrate the use of 8 differential amplifiers, but in some examples 19 referential amplifiers are shown. In FIG. 1, each of the pairs of electrode leads 11a–11h, preferably eight pairs of such leads, is connected to its own individual differential amplifier. As illustrated, the electrode pair 11a is connected to the amplifier 14a, the electrode pair 11b is connected to the amplifier 14b and the electrode pair 11h is connected to the amplifier 14h. As shown, if bipolar derivations are to be recorded directly rather than constructed by computation from monpolar recordings, preferably there would be eight differential amplifiers 14a–14h. This reduces the cost of the analog circuitry but sacrifices some of the spatial resolution available if 19 monopolar channels are used, computing bipolar derivations as specified but also providing monopolar information.

Each of the differential amplifiers 14a–14h has an input isolation switch to protect against current leakage; for example, a suitable isolation switch is a photo-diode - light-emitting diode (LED) isolation coupler. In addition, each amplifier input is protected from electrical interference by use of a radio-frequency filter and a 60-cycle notch filter. Preferably, each amplifier has a frequency range of 0.5 to 100 Hz, gain of 10,000, a common mode rejection of 160 DB, and noise of less than 2 microvolts. Such high-gain low-noise differential amplifiers are presently commercially available.

An alternative to the use of the eight bipolar derivations would be the direct use of the 19 electrodes of the monopolar International 10/20 system as inputs to 19 corresponding individual amplifiers. Each of the 19 inputs may be compared (referenced) against an inactive electrode such as an electrode connected to the earlobe. If desired, any bipolar derivations of interest could be constructed by computation.

The cardio-pulmonary bypass pump 30, which is a type of artificial heart-lung machine, is used in place of the heart and lungs of the patient during the operation to pump blood and to supply the blood with oxygen. Two on-line measuring transducers are connected to the pump 30. The blood flow transducer 31 provides an electrical output which corresponds to the blood flow in milliliters per minute. The temperature transducer 32 provides an electrical output corresponding to the patient's blood temperature as it flows through the pump 30.

An analog-to-digital multiplexer (A/D multiplexer) 33 provides a digital output from the various analog amplifiers and transducers which are connected to its input. The eight differential amplifiers, represented by 14a–14h, are connected to the A/D multiplexer 33, as is the blood flow transducer 31 and the blood temperature transducer 32. The A/D multiplexer 33 samples the EEG waves (outputs of differential amplifiers 14a-14h) at a rate which is compatible with the bandwidth of those amplifiers, preferably at the rate of 200 to 300 times per second to comply with their 0.05 to 100 Hz bandwidth. The sampling rate applied to the blood flow and blood temperature transducers would be at a lower rate.

In addition, other transducers may provide electrical information concerning the patient which may be sampled at an appropriate rate by the A/D multiplexer 33. For example, measuring transducers may be used whose output lines provide signals indicating body core temperature (thermistor, the patient's blood pressure, the electrocardiogram (EKG) and other patient parameters.

The information from the multiplexer is provided over line 34 to a microprocessor 35. The microprocessor has been programmed by an external software program means such as a floppy disk recorder or other input system 36. The microprocessor may be the INTEL 8086, NEC-PD8086 or the LSI 11-23, or other comparable devices.

The program and its controlled microprocessor condition the input signals and insure that they are valid biological signals. Such validity checks on the input signals include calibration and impedance measurements, and automatic artifact rejection algorithms.

CALIBRATION AND IMPEDANCE TEST

A preferred calibration system utilizes four sine wave generators 40-43 whose outputs are connected to each of the differential amplifiers. The generators produce sine waves at predetermined frequencies, preferably at 2.5, 5.5, 10 and 15.75 Hz. The sine waves suitably are at 20 microvolts peak-to-peak voltage and are mixed into a composite signal over a predetermined time period, for example, 5 seconds of the component signal are fed into each of the differential amplifiers. The composite sine wave signal is amplified by each differential amplifier, converted to a digital set of values by the A/D converter, subjected to spectral analysis and the results transferred to relative power, i.e., what is the percent of the power in each frequency interval. The relative power is then compared to the relative power calibration standard which has been predetermined and stored in the storage register 45. Preferably, the results of the relative power comparison for each channel (each differential amplifier) should be within plus or minus 5% of the unexpected value at each frequency. The operator calibrates by using button 56a on control-display panel 50, see FIG. 3. If the calibration shows an out-of-limit (non-calibrated) amplifier or a defect in the analysis system the warning light 56 will become lighted.

As explained in the applicant's prior U.S. Pat. No. 4,411,273 (Ser. No. 873,118), the impedance of each of the pairs of electrodes 11a-11h is automatically tested from time to time to ensure proper connection to the patient's scalp. Unacceptable high electrode impedance are reported by the warning lights 57.

MUSCLE ARTIFACT AND SPIKE DETECTION

The system will also provide a means of detecting muscle artifact and epileptiform spikes. The objective is to cancel, i.e., not use, those periods of brain wave activity which are contaminated with muscle or movement artifacts, which appear as noise relative to the desired brain wave signals, but to accept as valid those segments which contain signs of pathology. The number of brain wave spikes may be counted to provide useful information about epileptiform activity due to ischemia which may produce seizures and indicate the risk of brain damage.

In order to detect spikes and muscle artifact, six computations are dynamically performed on each EEG segment. These six computations are as follows:

Mean amplitude ($\overline{V}$), standard deviation of mean amplitude ($\sigma\overline{V}$), mean slope ($\overline{V}'$), and standard deviation of mean slope ($\sigma\overline{V}'$), means sharpness ($\overline{V}''$), and standard deviation of mean sharpness ($\sigma\overline{V}''$). [V' denotes dV/dt, and V'' denotes $d^2V/dt^2$ and sigma = $\sigma$].

After these six computations are dynamically computed, for each EEG segment in each derivation, confidence intervals are set for statistically significant deviations from Gaussianity (normal or bell-curve distribution). Reasonable definitions of such confidence intervals are $\overline{V}+3\sigma$, $\overline{V}'+5\sigma$ or 2 $\mu$V/ms, $\overline{V}''+6\sigma$. However, other confidence intervals may be found preferable during special conditions of anesthesia or CPB.

An estimate of a reliable sample size is preferably made as follows:

Under stable baseline physiological conditions, the system will take successive 2.56 second samples and perform the six computations, described in the paragraphs above, upon integer multiple samples (1, 2, 4 and 8 samples). The values of the 6 parameters ($\overline{V}$, $\overline{V}'$, $\overline{V}''$, $\sigma v$, $\sigma v'$, $\sigma v''$) will be compared, within each derivation, as the sample size is increased, i.e., AS 1,2,4, etc. such samples are combined, until these values stabilize. Stabilization will be defined as a t-test which is not significant between two successive parameter sets, i.e.

$$\frac{V_1 - V_2}{\sqrt{\sigma V_1^2 + \sigma V_2^2}} ; \frac{V'_1 - V'_2}{\sqrt{\sigma V'_1{}^2 + \sigma V'_2{}^2}} ; \frac{V''_1 - V''_2}{\sqrt{\sigma V''_1{}^2 + \sigma V''_2{}^2}}$$

The system will then notify the operator as to the size of a "reliable sample" under current conditions. This will determine the minimum update time during monitoring. Data will continue to be gathered in 2.56 segments, combined to achieve the required size, and the test parameters derived from the "reliable sample" size will be applied to evaluate each such reliable size segment.

If, in any of the six derivations, the voltage value $V_t$ for any time point exceeds $\overline{V}+3\sigma$ or the slope $V'_t$ exceeds $\overline{V}'+5\sigma$, the segment will be considered "suspect". The "reliable sample" waves are displayed on CRT display 58.

For any time point a "suspect" segment will contain a "spike" if it (i) contains a component whose sharpness $V'''_t$ exceeds $\overline{V}''+6\sigma$, (ii) contains a component whose rising and falling slope V' exceeds $\overline{V}'+5\sigma$ or 2 $\mu$V/ms, (iii) contains such a component whose duration lies between 10 and 80 ms from the time its amplitude V exceeds $\overline{V}+2\sigma$ until it returns to $\leq \overline{V}+2\sigma$, and (iv) does not contain another such component within 200 ms. Events occurring within 200 ms of the beginning and end of each segment must be disregarded.

Figure 3:
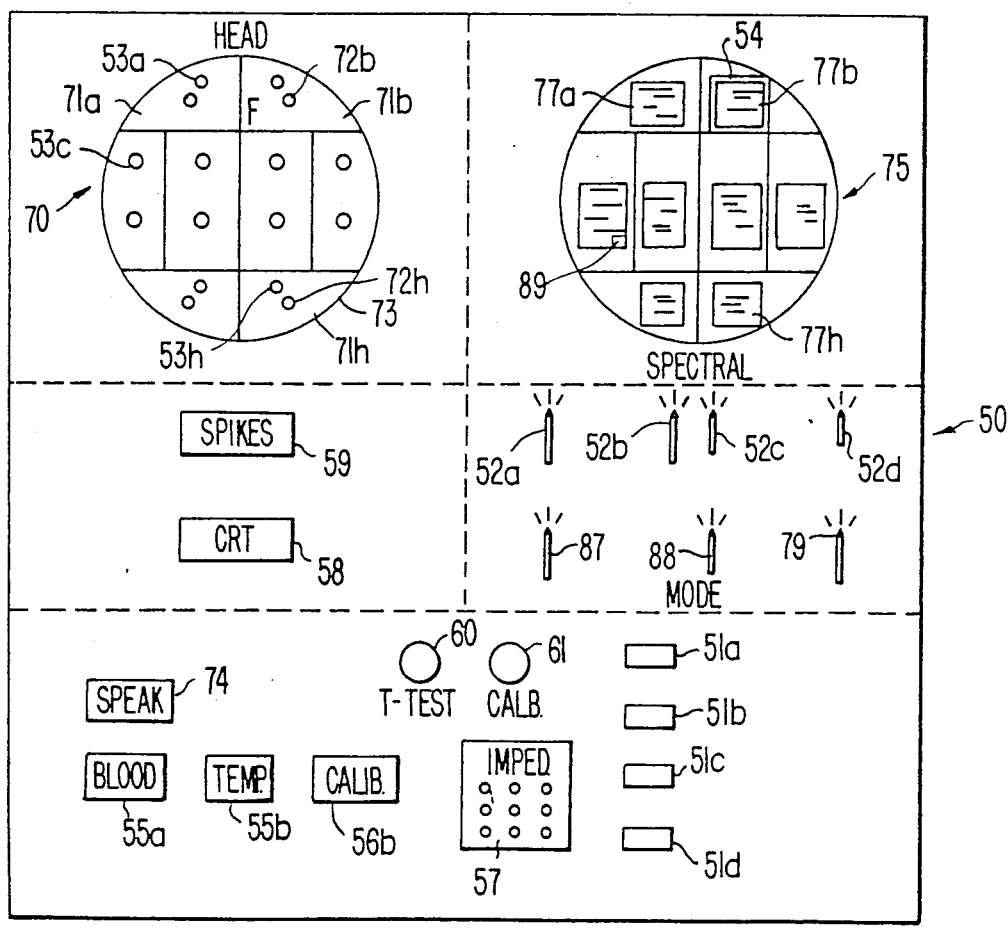
FIG. 3 is a front plan view of the proposed control and bipolar display panel for use in the system of FIG. 1; an analogous display, now shown, would represent the 19-channel 10/20 System.

The display, on the display panel 50, shown in FIG. 3, includes a spike counter 59, which is a numerical digital display which accumulates total number of spikes in each region.

Unless all of the conditions as to a "spike" are satisfied by the detected suspect segment, the departure from Gaussianity (bell curve) will be interpreted as either muscle artifact (MA) or movement artifact, and the segment will be rejected. If all the conditions for a "spike" are satisfied, or if none of the above conditions are detected, the segment will be classified either as an acceptable EEG signal containing an epileptiform spike or an acceptable EEG signal containing no paroxysmal episode. In either case, the segment is accepted for further processing.

DATA ANALYSIS

A "derivation" is the data in one channel, i.e., from one differential amplifier, and a "derivation segment" is the data collected over a period of time (minimum 2.56 seconds; max, 25.6 seconds) for a reliable sample. "Update time" depends on reliability of data.

If any derivation segment from any of the eight derivations is rejected as artifact, the entire segment (all derivations) is rejected. If all the segments are accepted (all eight derivations), evaluation of the valid biological data continues as follows:

For each accepted segment i recorded from all 8 derivations, the digitized data will be stored in individual scratch registers $60a-60h$. Assuming a sampling rate of 200/sec and a maximum segment length of 25.6 sec. with the storage capacity of each scratch register $60a-60h$ being 5128 words then for the 8 derivations 41.024K words of memory will be occupied per raw segment. Each word is 1-3 bytes, depending upon the microprocessor which is used.

For each "derivation segment", a flag bit (an output signal) will be raised if a spike was detected. The spikes will be counted and displayed on the visual display 50 at digital counter 59.

A Fast Fourier Transform (FFT) will be performed on each derivation segment, preferably using an FFT chip 47.

The actual power spectral values yielded by the FFT of each derivation segment, between 0-100 Hz, will be stored in a series of scratch registers $68a-68h$, each of whose size may be 2.4K (coefficient, sine, cosine terms for each frequency $\times 8$ derivations).

The absolute power and the percentage of relative power is computed for the following brain wave frequency bands: low delta (0.5-1.5), high delta (1.5-3.5), theta (3.5-7.5), alpha (7.5-12.5), low beta (12.5-25), high beta (25-50) and gamma (50-100) (all in Hz). The power data are subjected to Z-transformation; for each feature the differences between the patient's values and the mean for the normal group is divided by the standard deviation of the normal group. The 8-transformation method characterizes the deviation of the subject value from the normal outcome mean value (or any other norm which is selected) as a number of standard deviations (error steps). The "normal group" is the normal outcome group.

The formula is:

$$Z = \frac{X - M}{\sigma x}$$

where the number of error steps, 8, is representative of a particular neurometric invariate or multivariate index and equal to the difference between the patient's index value for that feature, X, and the means value of the appropriate reference group or norm, M, divided by the standard deviation of the whole sample, $\sigma x$. The total sample standard deviation is computed according to:

$$\sigma X = \sqrt{\Sigma(x - \bar{x})^2}$$

where X is the patient index value and $\bar{x}$ is the average index value of the appropriate normative data.

The effect of the 8-transform is to provide the common metric of relative probability as the dimensions or units in which all features are stated. Relative probability means the probability of obtaining the observed value by chance in a member of the sample from which the reference was constructed.

A set of thresholds, based on selected norms, is established; for example, one type of norm is established by evaluation of a group of cardiovascular surgical patients (control group), whose post-operative recovery was without neurological complications, under representative conditions of premedication, anesthesia and CPB. The set of norms provides the criteria for what is considered to be "abnormal", absolute or relative power in high delta, theta, alpha, low beta, low delta, high delta, gamma, frequency bands. Abnormal coherence or asymmetry between symmetrical derivations and abnormal total power may be obtained.

The norms which may be selected include—but are not limited to:

(1) population norms—age regression equations for the normal unanesthetized patient (used for preoperative screening)

(2) self-norms obtained from the individual patients before anesthesia and before the operation (used as a comparison to assess the anesthetic procedure or the effect of non-pulsatile flow at normal rates and temperatures.

(3) post-anesthetic and pre-operative (used to assess the effect of the anesthetic and the patient's non-pulsatile flow at normal flow rates and temperatures). These are self-norms.

(4) the patient's self-norms after being anesthetized and while on the heart machine (CPB)—(used to assess the effect of non-pulsatile flow). The CPB is at normal flow and temperature.

(5) "pump-patient relationship norms" derived from groups of previous patients of approximately comparable age to the present individual patient at each pump flow rate and blood temperature, all of whom displayed no neurological dysfunctions or cognitive-emotional impairment following successful CPB procedures (used to identify brain changes beyond the limits predicted by the "pump-patient relationship" set forth below). The "pump-patient relationship" describes the purely biophysical effects of cardiopulmonary bypass.

(6) population norms for specific intraoperative conditions while using the CPB—(to gauge the clinical significance of observed changes). For example, the conditions may include (a) specific anesthetic agents—the effect of a particular anesthetic agent may be general and different from another anesthetic agent, (b) the reaction to specific changes in pump flow rate and changes in temperature (rates of changes).

The age-regression equations, population norms and pump-patient relationship described above provide the mean (M) and standard deviation ($\sigma$) of every quantitative group of features for a group of persons who are the same age as the patient. They may be either normal healthy unanesthetized subjects or patients who had CPB without subsequent complications. The "self-norms" will be computed as follows:

1. The reliable sample size will be determined by the operation described above;

2. Preferably twenty-four samples of reliable size will be gathered. As each sample is gathered, the measures which have been optionally selected will be quantitatively extracted and stored on the scratch pad memory 61. The raw sample will be deleted;

3. After 24 reliable samples have been gathered, the mean (M) and standard deviation ($\sigma$) of each measure will be computed across the set of 24 samples. These values of M and $\sigma$ will define the self-norm.

The "pump-patient relationship" of the present invention predicts the percent change in neurophysiological processes attributable to the biophysical consequences of reduced blood volume per unit time, and reduced temperature.

$$\% \text{ change} = A\left[\frac{T_N - T_P}{10}\right] + B\left[\frac{V_N - V_P}{V_N}\right]$$

where $T_N$ = normal body temperature, 37° C.
$T_P$ = perfusion blood temperature
$V_N$ = normal perfusion volume
$V_P$ = current pump perfusion volume A and B are coefficients and fractions required to scale the parenthetical values to appropriate percentages. A is in the range 0.4 to 0.6 and preferably 0.5; B is in the range 0.2 to 0.5 and is preferably 0.4.

The data is also analyzed as to its statistical significance. It is important not only to know how different one group of data is from another, but also what is the likelihood that the difference is meaningful and not just a matter of chance. The "t" test is used to indicate the degree of confidence that the data are not due to chance.

The "t test" or "Students t test" is a statistical test for the measure of the significance of the difference between two sample populations (here, conditions x and y) and provides a selected degree of statistical confidence ("P"). For example, it may indicate a high level of confidence, i.e., that the brain "very likely" responded differently to two stimuli. The "very likely" may be P=0.001, which indicates the result occurring by random chance is 1 in 1000.

The t-test computation is $$t = \left| \frac{\frac{\Sigma x}{N_x} - \frac{\Sigma y}{N_y}}{\sqrt{\frac{\sigma x^2}{N_x} - \frac{\sigma y^2}{N_y}}} \right|$$

where x and y are the two conditions being measured, N is the sample size, $\Sigma$ is the sum and $$\sigma x^2 = \frac{\Sigma x^2}{N_x} \left(\frac{\Sigma x}{N_x}\right)^2$$

Absolute total power and relative (percent) power will be computed for each derivation segment in each frequency band (alpha, low beta, high beta, low delta, high delta, gamma and theta). Coherence and symmetry will also be computed for each frequency band between homologous pairs of derivations.

After data reduction, each derivation segment will be evaluated against the selected set of norms (explained above) using one or more of the following options. The options are selected by the switches 52a–52d on display panel 50.

1. Absolute power spectrum, coherence and symmetry (switch 52a);

2. Relative power spectrum, coherence and symmetry (switch 52b);

3. Absolute power (switch 52c) or relative power (switch 52d) in high delta, theta, alpha and beta frequency bands will be tested for whether it is beyond the mean value±2$\sigma$, relative to any selected set of norms.

The "possible abnormality" visual indicator lights 51a–51b will light with each light 51a–51d corresponding to a respective frequency band on the display panel 50 when the content of any band in any head region is beyond the threshold limit. In addition, an "alarm" light, preferably red LED 53a–53h, will light in a flashing on-off manner in the corresponding head sector. Alternatively, if a full array (window) 77a–77h is displayed its rim 54 will flash on-off in red for an "alarm" signal, see FIG. 3.

It is presently believed that excessive low delta probably reflects muscle movements, excessive high beta probably reflects muscle artifacts, and excessive gamma probably reflects environmental noise which may have eluded the artifact rejection and noise suppression means. Preferably, data of "questionable validity" should be accepted contingently and so indicated by lighting indicators 51a–51d with on-off flashing; while possible non-cerebral sources for the excessively high levels are sought.

DATA DISPLAY

The results of data evaluation are preferably displayed in two ways: (i) normal-abnormal head diagram 70; and/or (ii) intensity-modulated topographic spectral arrays 75; and/or (iii) EEG traces of current 2.5 sec. EEG traces.

Normal-abnormal indicators and intensity-modulated spectral arrays may be superimposed as a single display, or may be two separate displays. By a toggle switch, the EEG tracings may be superimposed on the spectral arrays or viewed alone.

A. Normal-abnormal head diagrams

On the instrument panel 50, an outline of a head is depicted seen face upward. The head is divided into eight sectors 71a–71h with each sector corresponding to each derivation. Each sector 71a–71h contains a light indicator 72a–72h such as an LED (light-emitting diode).

If a current EEG segment for a derivation is evaluated as within normal limits (using options selected in Data Analysis), the indicator LED 72a–72h will be green. If the segment is found to be abnormal, the LED will be red. If a spike, or spikes, was formed in a derivation segment, the corresponding LED will flash red at 1 second intervals. If any derivation is red for 2 successive segments, a tone speaker 74 will beep. If the derivation remains red for more than 1 minute, the pitch of the tone will rise.

B. Intensity-modulated topographical spectral arrays

On the panel 50, a second head diagram 75 is presented on a black-and-white color monitor 76. This idealized head 75 is divided into 8 sectors 77a–77h corresponding to the 8 bipolar derivations (or alternatively the 19 monopolar sectors, if desired). The "lines" are horizontal stripes (elongated areas). The optimal sample size might be larger or smaller. Each line represents the result of a spectral analysis (FFT) of an EEG segment of reliable size for the patient currently under evaluation. The line may represent the full spectrum, five absolute power frequency bands, four relative power frequency bands, coherence or asymmetry within the four bands or any set of measures selected from the quantitative options on the control panel by the switch 79. These measures are arranged in an orderly way from left to right along the line. The value of each measure is represented on a gray scale, ranging from black, which might correspond to 0 voltage or 0 percent or p=not significant, to white, which might correspond to maximum voltage (calibration scale at side of head) or 100 percent or p=extremely significant, see FIG. 4.

For example, as shown in FIG. 4, assume the samples 80a–80x represent the actual power frequency spectrum of reliable EEG segments with each line sample representing a measure of a segment. Each pixel from left to right would represent the actual power found in that EEG sample from 0 to 50 Hz as a shade of grey between black and white. As each sample is acquired and analyzed, it displaces the previous line upward. Thus, if a reliable sample required a 10-second sample, 24 horizontal lines would describe the last 4 minutes of EEG analysis, with the most recent 10 seconds 80a at the bottom of the stack and the oldest sample at the top 80x. This stack 80 of samples represents a window. As each successive segment is recorded and analyzed, it will be evaluated against the set of statistics (the M's and $\sigma$'s which the operator selected as the most appropriate norm). The window moves so that it is "on-line", i.e., includes the most current data. In the example illustrated in FIG. 4, the power in the samples 80b–80x is centered at about 25 Hz while the power in the segment 80a is centered at about 30 Hz. Each sector of the head display 75 has a window display stack 77a–77h of the type shown in FIG. 4.

A window of 24 reliable samples will be continuously updated. As the 25th sample is obtained, the first is dropped out of the window, as the 26th is obtained, the 2nd is dropped, etc. For each feature in every derivation, $M+\sigma$ are continuously updated across the most recent 24 samples. This will be referred to as a "continously updated norm". As soon as the first such set of norms is defined from the first 24 samples, a t-test will be performed between each subsequent segment and the previous 24, using the current values of M and $\sigma$. If a significant difference is detected, the window stops being updated. The values of M and $\sigma$ are stored and a new window begins to be constructed, accumulating the next 24 samples. Each sample continues to be t-tested against M and $\sigma$ of the window up to the point of detected instability or change. Each segment t-test result is reported separately. When the full new window of 24 samples has been gathered, a t-test is performed between the window before change was detected (NORM n) and the current window (NORM n+1). If the two windows are significantly different, the visual alarm 82 will be lighted or a buzzer 83 will sound.

The storage registers 84a–84h store the updated window norms (NORM n) and (NORM n+1) corresponding to the window. An updated norm can be constructed at any time and stored. This might be used to construct an updated self-norm for every stage within a CPB procedure, such as a change in pump flow rate or perfusion fluid temperature.

As an example, assume the 25th sample is significantly different from the 24 previous samples in the window. The 24 lines of the stack 85x–85b, corresponding to the 24 samples of the window, are replaced by one line 86 representing the average values of the previous 24 line window, as shown in FIG. 5. The new line 85a, significantly different, appears below the previous window average. The software window stops continuously updating and a new window is opened with the significant finding as the first line below the average of the previous window. That head sector begins to "blink" once per second. Successive samples are compared to the previous window norms, "NORMS"$_n$. If the difference is not significant, the blinking stops. If it remains significant, the blinking resumes. When the full new set of 24 reliable samples fills the window, a formal test of significance is performed between NORMS$_n$ and NORM$_n$+1, constructed from the M & $\sigma$ of features in the last 24 samples. If the two sets of data are significantly different at the selected p-value, a visual alarm 96, or auditory alarm, will inform the operator.

The operator may expect the state change which has been detected because of a known deliberate clinical maneuver, e.g., change in pump flow rate. He may then elect to replace the previous NORMS$_n$, as more appropriate, by operation of switch 87. He may wish to compare the new NORMS$_n$+1 to some other baseline, such as "postanesthesia self norms", before make a decision. A switch 88 on the panel would select a prior alternative norm set and appropriately report this on the head display. He may not have been previously aware of the change in state, institute a corrective procedure, and watch the state change back until it is no longer different from NORMS$_n$ (this implies NORMS$_n$+2 will not be different from NORMS$_n$).

In this embodiment a "spike detector", for each sector, may be a small square which will blink to indicate the presence of spikes in that sector, as shown at 89 in FIG. 3.

Alternatively, and not shown, the value of each measure may be displayed on a color scale, instead of the gray scale display of FIGS. 4 and 5. The horizontal "lines" (which are elongated rectangles) 80a–80x are color-coded, as described below.

C. Alternative Simplified Display of Windows of Norms

A further alternative embodiment is shown in FIG. 6 to replace the spectral arrays 75 of FIG. 3. In this embodiment the analysis and comparison associated with the moving window is the same; however, the results are displayed in a simplified form. The head diagram 90 is divided into eight sectors 91a–91h, each of which has three color-coded lights, for example, LED's; preferably blue or green 92a–92h; amber 93a–93h; and red 94a–94h. In each sector blue lights, when lighted, would indicate that the comparison shows a significant decrement in activity; an amber light when lighted would indicate that the latest sample (most recently taken sample) was not significantly different from the average of the samples (for example 24) of the prior window; and the light of a red lamp would indicate that the two windows (NORM$_n$) and (NORM$_n$+1) show a significant increase in activity.

D. Alternative Head Display Using Dots In Boxes

In this third display alternative embodiment, the results are displayed on three levels, which for the purpose of this description will be considered three planes. The viewer may select to view one of the three levels at one time; or may view any 2 or 3 levels superimposed upon each other. A suitable display is preferably produced on a high-quality color CRT monitor.

Figure 8:
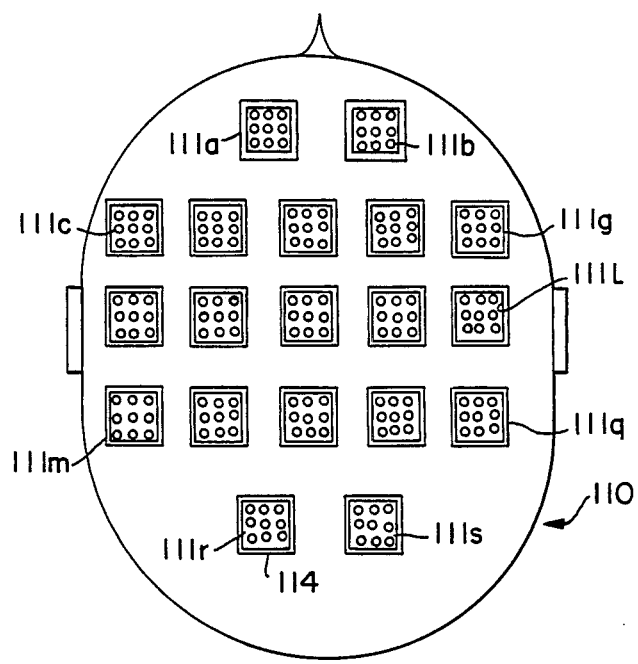
FIGS. 8 and 10–12 are top plan view of the third embodiment of the display of the present invention.
Figure 9:
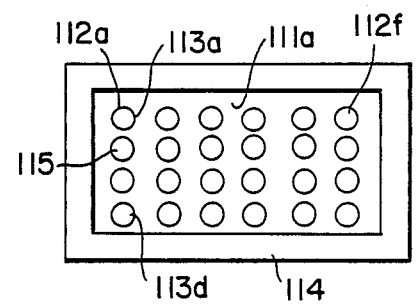
FIG. 9 is an enlarged top plan view of one block from FIG. 8; the number of rows can be expanded.

The first level (top level), illustrated in FIGS. 8 and 9, shows the outline of a head face-up 110 and a series of boxes 111a–111s. A typical box 111a is shown in FIG. 9. Each box corresponds to the head location in a topographic map. There are, preferably, 19 boxes arranged in 5 rows, starting from the front (top of map), with 2,5,5,5,2 boxes in the rows. These boxes correspond to the 19 electrodes of the International 10/20 Electrode Placement System. Each box contains a matrix of dots or line segments with R rows and C columns, within a frame; for example, there are four rows and six columns, as shown in FIG. 9. Each of the columns 112a–112f represents different measures, for example, for 6 columns the percentage of power in six different frequency bands. Each row 113a–113d represents the value of those measures extracted from sequential EEG segments of preselected duration. The boxes are shown in FIG. 8 with 3 columns and 3 rows only for simplicity of illustration. The rows within the matrix present a historical "scroll" type of information, with the latest data in the bottom row and moving up one row each time a new sample of data is analyzed. There might be a much larger number of rows, spanning a much longer period of observation, or history.

The frame 114 around each box represents a multivariate evaluation across the total set of current values, correcting for intercorrelations between measures (mahalanobis distance). Each box gives information by (i) the color of its frame 114, and (iii) the colors of the dots 115 (rows and columns within the box. For example, after each EEG segment is evaluated, the frame color indicates the total multivariate abnormality; when that degree exceeds some preselected level, the frame flashes on and off. Examples of color coding might use a "heat scale", with light blue as highly abnormal, ($P<0.01$, less than reference norm), blue as slightly abnormal ($P<0.05$ less than reference norm), gray as normal, red as slightly abnormal ($P<0.05$, more than reference norm), and yellow as highly abnormal ($P<0.01$, more than reference norm). The same colors should be used to encode statistical significance of univariate and multivariate measures, i.e., abnormal values of both the dots and frame are encoded identically. FIG. 8 is shown with a 3×3 matrix of dots, in each box, for the purpose of illustration only, but preferably a larger number of dots are used, for example, a 4×6 matrix, as shown in FIG. 9, or even 4×40. The vertical number can be selected by the operator.

Figure 10:
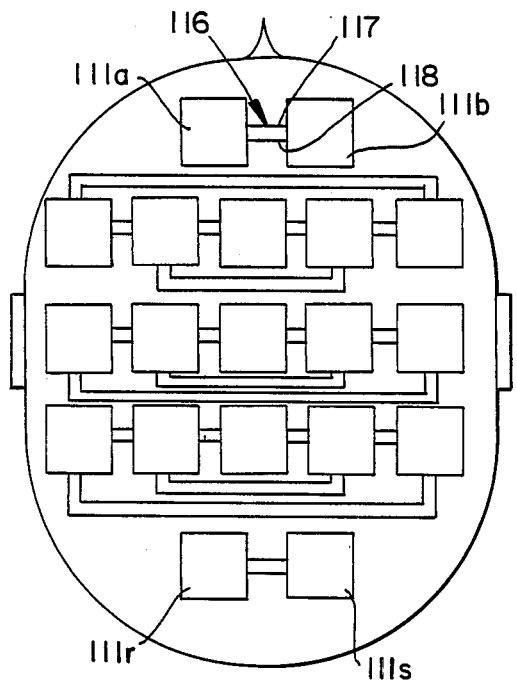

The second level, shown in FIG. 10, provides horizontal cross-measures 116 of the coherence (synchronization) and power ratio between brain locations in the same coronal plane. Such measures of relationship between different brain regions are often as important, or more important, than measures describing variables within a specific location. Two horizontal bars 117 and 118 (lines) link each pair of regions. The upper bar reports the coherence and the lower bar reports the power ratio. In rows 1 and 5 the two boxes 111a and 111b and 111r and 111s, respectively, are cross-linked; in rows 2,3,4 the outer boxes are cross-linked; the inner two boxes (next to the outer boxes) are cross-linked. These linkages are between "homologous" or symmetrical regions. In addition, there are linkage bars between adjacent boxes. The degree of abnormality of any of these relationships is color-coded in the bars, like the information in each box.

Figure 11:
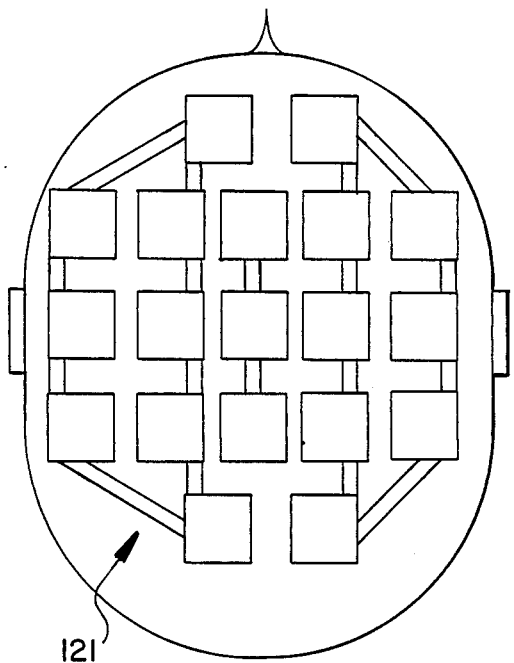
Figure 12:
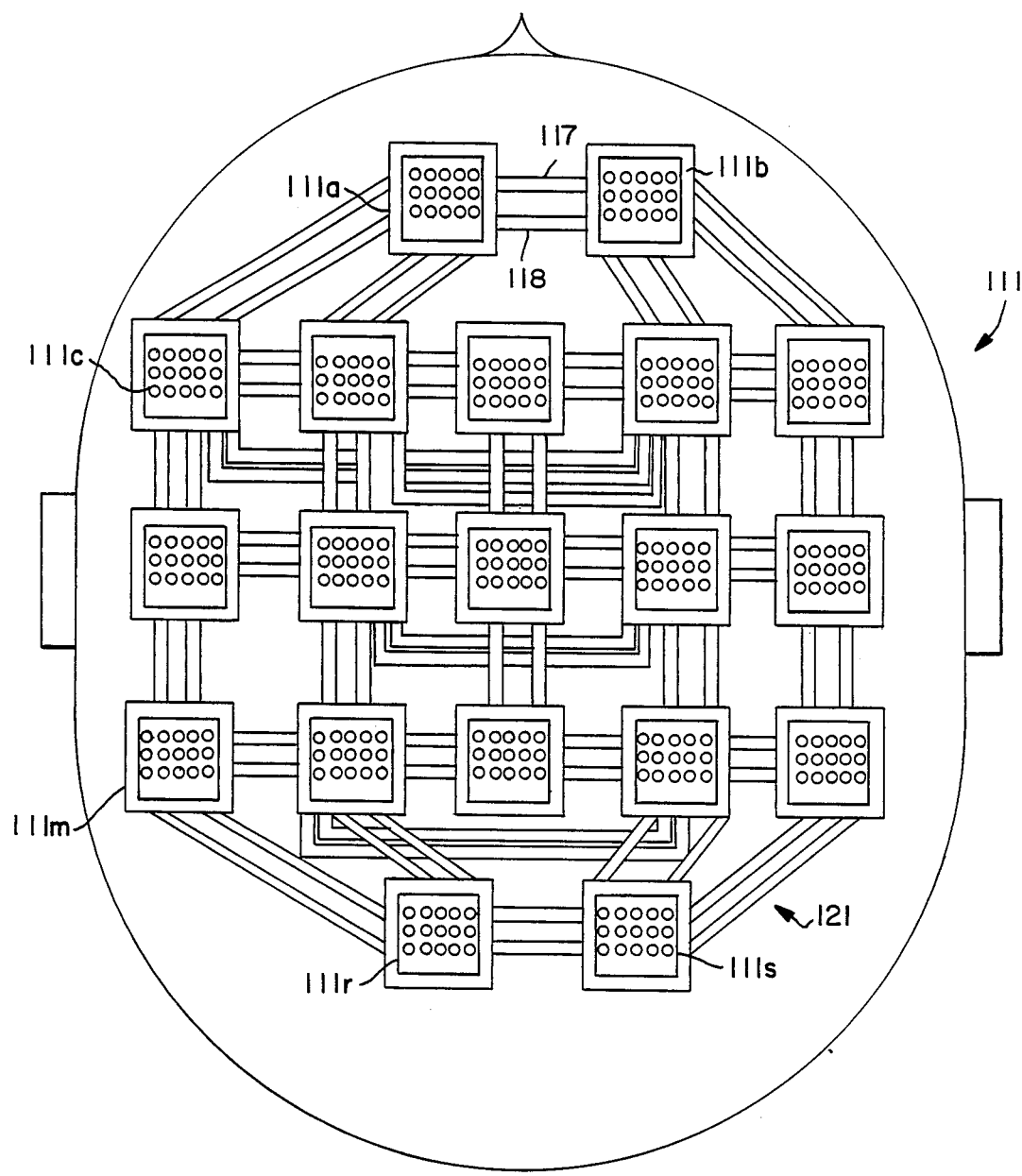

A similar cross-linking colored bar structure 121 is used to show the anterior-posterior relationship between brain locations. As shown in FIG. 11, there are two bars (lines) between each box and its vertical neighbor. The lateral of these bars reports the synchrony, while the medial reports the power ratio between neighboring regions. The color-coding of abnormality is like that of the other measures. FIGS. 10 and 11, for purpose of clarity of illustration, omit the dots within each box and omit the frame around each box; however, in practice the dots are within the boxes and the frames are around the boxes in the actual display, as shown in FIG. 12.

E. Alternative Head Display Using Tiles

Figure 13:
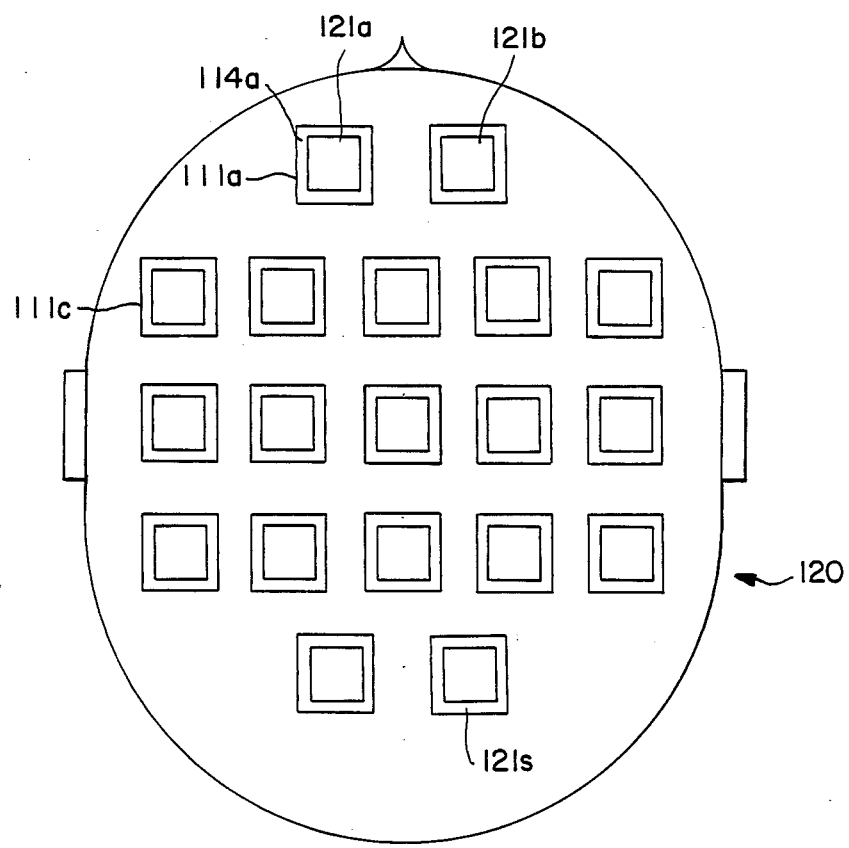
FIG. 13 is a top plan view of the fourth embodiment of the display of the present invention.

A still further alternative embodiment is shown in FIG. 13. In this embodiment the quantitative analysis and statistical comparison associated with the moving window of FIGS. 4 and 5 may be the same; however, the results are displayed in a simplified form. The display is similar to that of FIG. 6 but, instead of lights, such as LED's, the display uses block areas (called "tiles" herein) on a TV (video) color monitor. The head diagram 120, shown on the monitor, is divided into nineteen sectors 121a–121a, each of which is a tile (block) which is color-coded.

A color, as in the prior embodiments using the video monitor, uses the "heat" spectrum of colors. For example, when a tile is blue it indicates that the comparison shows significantly less activity than the reference norm; an amber color indicates that the most recent sample is not significantly different from the average of the n samples (for example 24) of the prior window; and the red color of the tile indicates that the most recent sample shows significantly more activity than the reference norm.

As in the prior embodiment of FIGS. 8–12, possibly but not preferably each title (block) is surrounded by a frame (border) which may blink in case of an alarm (not shown). If desired, the tiles (blocks) may be connected by bars, as in the embodiment of FIGS. 10–12 and shown on three different levels and superimposed as in FIGS. 10–12.

F. Alternative Head Display Showing Brain Wave Coherence

Figure 15:
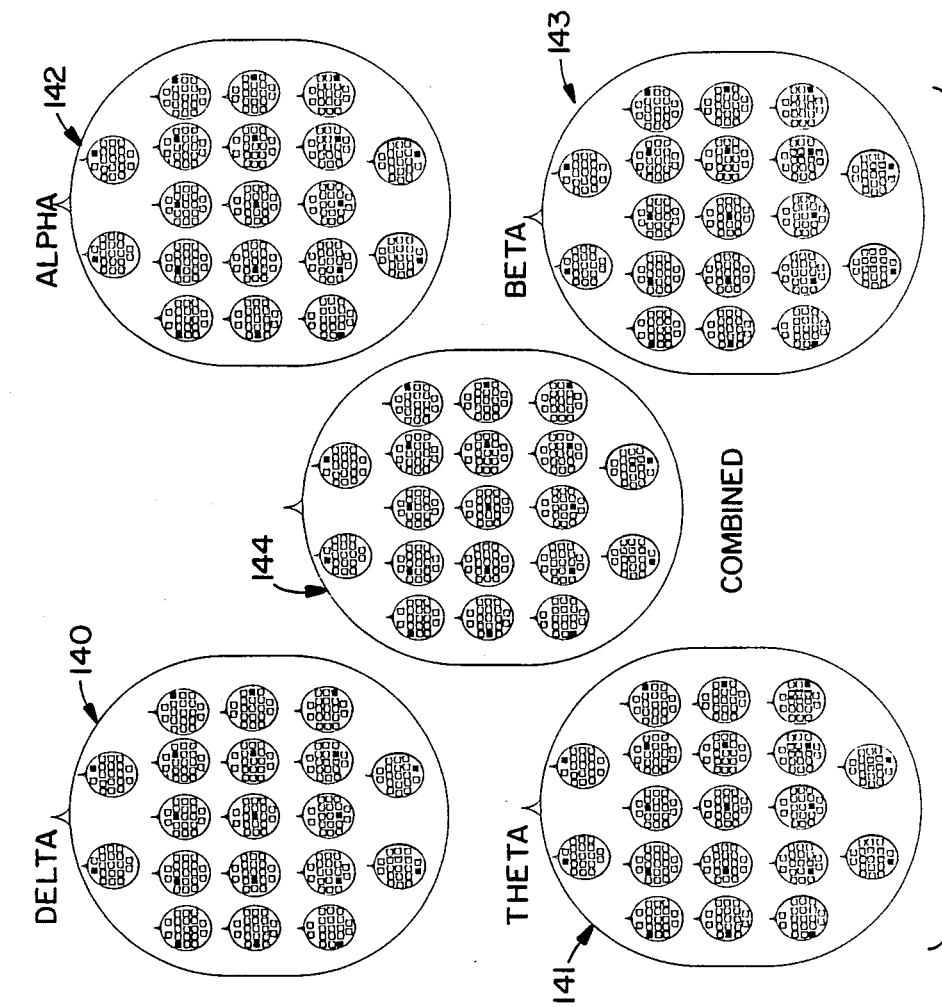
FIG. 15 is a top plan view of the fourth embodiment of the display of the present invention.
Figure 14:
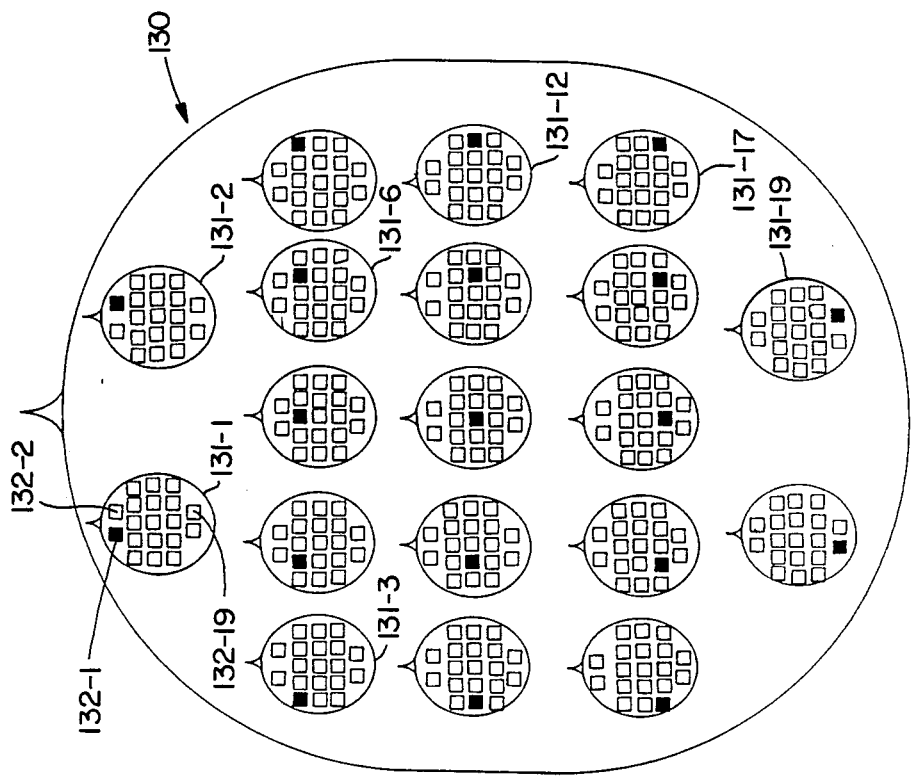
FIG. 14 is an enlarged view of one head map from FIG. 15.

An alternative embodiment of the present invention showing a topographical head display is shown in FIGS. 14 and 15. FIG. 14 shows the display of a single measure, for example, the coherence of the patient's brain waves in the delta band. Each of the 19 electrodes, according to the 10/20 system, is connected to a different sector of the patient's head to monitor brain waves in that region. This is shown in one overall head-like FIG. 130, preferably displayed in color on a CRT monitor. Within the FIG. 130 there are 19 head-shaped smaller figures, arranged to correspond to the 19 electrode positions, labeled 131-1 to 131-19. Each smaller head display, 131-1 to 131-19, shows the coherence between brain waves at the electrode located in that position and the other 18 electrodes. Each of the 19 electrodes corresponds to one of the 19 small squares ("dots"), 132-1 to 132-19 within each small head display, also arranged to correspond to the 10/20 system. For example, the statistical significance of the coherence between the electrode (head location) 131-1 and the diametrically opposite electrode 131-19, in the absolute power in the delta band, is shown by the color of the small square 132-19 in the head diagram 131-1. The Z-score of absolute power for the locus of the small head display is encoded in the "fiducial" position; that is, the corresponding position on the small head, shown by the black square on each small head in FIG. 14. This information is essential in order to evaluate the amount of power for which the coherence is being computed.

A more complete display is shown in FIG. 15. Each of the 5 large head maps is for a different measure. For example, the measures are absolute power in the delta frequency band (0.5–3.5 Hz) in head diagram 140; theta band (3.5–7.5 Hz) in head diagram 141; alpha band (7.5 to 12.5 Hz) head diagram 142 and beta band (12.5–50 Hz) in head diagram 143 and the entire frequency band (combined delta, theta, alpha and beta) in head diagram 144. As explained above, the power data is automatically Z-transformed by the computer system and compared to normative values in the computer memory. The color of every entry in each small head encodes the degree of abnormality, at the head position corresponding to that electrode for the coherence with each of the other 18 head positions.

Preferably the color is related to the normal or Gaussian distribution ("bell curve"). The dot (square) representing the electrode position is color coded to reflect the Z-score of the absolute power in that frequency band in that electrode position.

G. Alarms

During an operation a comparison is made between the current sample and the rest of previous (current) window and norms. (1) If significance threshold exceeded, an "alert" state is entered (red or blue light or sector outlined in red or blue); (2) The sliding window collapses into M and $\sigma$; across previous n segments in sample (3) New window (group) is constructed, with each segment tested against M and $\sigma$ from previous group. The alert is maintained or reversed; (4) If the alert is maintained, a t-test is performed between window N & N+1.

If the t-test shows that the difference between N and N+1 is significant, an alarm light 60 will be lighted, or alternatively a buzzer will sound. Preferably, a different warning light 61 is used to alert that the calibration of the differential amplifiers is unsatisfactory. The warning lights of the panel of lights 57 warn that the impedance of the electrodes is unsatisfactory, with each light on the panel 57 corresponding to an electrode, see FIG. 3. For the "alert" state the red or blue light is shown in FIG. 6 and the sector outlined in red or blue is shown in FIG. 3.

A PROGRAMMED KEYBOARD AND USER OPTIONS

In FIG. 7 an additional control panel (keyboard) is illustrated which has a number of programmed keys (function keys). Each such key, which is labeled with its function, when activated, will call up a small control program from the microprocessor's memory and effectuate the program. The "enter choice" key may be the normal "return" key of the microprocessor. For example, when the key F1 "calibrate amplifiers" is depressed the program will in turn calibrate each of the differential amplifiers, as explained above.

The system is "menu driven" i.e. before the acquisition and analysis data begins the user must select from a series of options from a "menu", i.e., list, displayed on the CRT screen 75. The menu options are discussed in detail below. But, for example, when the user operates function key F9, which constructed a norm, the norm has been pre-selected by the user from the menu. So when the user operates function key F9 the norm constructed may be, for example, the self-norm for the patient when pre-operative and conscious. The operation of the function key F9 will automatically begin the construction (data collection and analysis) for that norm.

The following is the preferred "menu". Each group provides a choice of options. For example, under "Bandpass" (frequency range) the user may select "9" or "10" which provides 1–50 Hz or 1–100 Hz respectively. The user will select one or the other, before the data is started to be collected, by depressing "9" or "10" on the numerical key pad 81.

Preferably, 19 of the function keys are programmed as follows:

| | |
|---|---|
| F1 | CALIBRATE AMPLIFIERS |
| F2 | ELECTRODE IMPEDANCE TEST |
| F3 | RECORD EEG (recorded on floppy disk or other recording media) |
| F4 | DISPLAY EEG (8 channels-on line), or toggle for superposition on head F6, |
| F5 | DISPLAY SPIKES (their waveshapes, not number) |
| F6 | DISPLAY HEAD PICTURE #X, (type desired #) |
| F7 | DISPLAY TRAJECTORY #X, (type desired #) |
| F8 | CHANGE REFERENCE NORMS TO #X, (type desired #) |
| F9 | CONSTRUCT NORM #X, (type desired #) |
| F10 | DISPLAY t-TEST AGAINST NORM #X vs. NORM #Y, |
| F11 | DISPLAY t-TEST NORM #X vs. NORM #Y, |
| F12 | REPLAY FROM $T_1$ (00:00:00) to $T_2$ (00:00:00) |
| F13 | DISPLAY MENU ON VIDEO |
| F14 | PRINT VIDEO (read out) |
| F15 | BEGIN #X (CONDITION X) |
| F16 | END #X (CONDITION X) |
| F17 | DISPLAY [L #X-R#X] |
| F18 | AUTOMATIC RETURN TO PRIOR-CONDITIONS AFTER TIME LAPSE |
| F19 | AUTOMATIC ALARM |

MONTAGE

1. Whole head EEG, 8 channels bipolar (+ EKG, BP, RGCP)
2. Left hemisphere, 8 channels monopolar
3. Right hemisphere, 8 channels monopolar
4. Front of head bilateral, 8 channels monopolar
5. Back of head bilateral, 8 channels monopolar
6. Whole head bilateral, 8 channels monopolar $F_{P1}/F_{P2}$, $F_7/F_8$, $T_3/T_4$, $T_5/T_6$
7. Whole head medial, 8 channels monopolar $F_3/F_4$, $C_3/C_4$, $P_3/P_4$, $O_1/O_2$
8. Whole head, 16 original channel monopolar-optional

| | BANDPASS | | EPOCHLENGTH |
|---|---|---|---|
| 9 | 1–50 Hz | 11 | 2.56 sec |
| 10 | 1–100 Hz | 12 | 5.12 sec (2 × 2.56) |
| | | 13 | 10.24 sec (4 × 2.56) |
| | | 14 | 20.48 sec (8 × 2.56) |

NORMS

15. AGE REGRESSION EQUATIONS
16. SELF NORM-PATIENT CONSCIOUS (pre-operative or experimental baseline)
17. SELF NORM-PATIENT ANESTHETIZED (pre-operative)
18. PREVIOUS MINUTE, MOVING WINDOW
19. PREVIOUS 5 MINUTES, MOVING WINDOW
20. PUMP-PATIENT RELATIONSHIP, FULL FLOW, 37°
21. PUMP-PATIENT RELATIONSHIP, ACTUAL FLOW AND TEMP
22. SELF-NORM-CONDITION X (STRIKE X ON KEYBOARD), WHERE X MAY BE AN EXPERIMENTAL CONDITION IN A CONSCIOUS PATIENT

ARTIFACT REJECTION

23. AMPLITUDE THRESHOLD (STATIC)
24. GAUSSIANITY TEST (DYNAMIC)
25. SUBTRACT CURRENT EKG SPECTRUM (ABSOLUTE POWER)

```
                (BEFORE DISPLAY OF DATA)
                    NORM CONSTRUCTION
24  COMPUTE 'SELF NORM, CONDITION X' WITHIN
    ANY PATIENT INDICATED BY 'BEGIN 1-END 1',
    BEGIN 2-END 2, ETC.
25  STORE RESULT OF 24 ON NORM OR POPULA-
    TION DISK OR SESSION DISK
26  COMPUTE MEANS & SD ACROSS TOTAL SAMPLE
    ON POPULATION DISK-'POPULATION NORM,
    CONDITION X'
27  DISPLAY MATRIX 24
28  DISPLAY MATRIX 26
29  STORE RESULT OF 26 ON PROGRAM DISK,
    IDENTIFIED AS POPULATION NORM, CONDI-
    TION X EKG, EP, RESP DIGITAL DISPLAY ON TOP OR
    BOTTOM
            DISPLAY SELECTION-HEAD PICTURES
30  DENSITY OR COLOR CODED SPECTRAL ARRAY,
    ABSOLUTE POWER
31  DENSITY OR COLOR CODED BAND ARRAY, ABSO-
    LUTE POWER
32  DENSITY OR COLOR CODED SPECTRAL ARRAY,
    RELATIVE POWER
33  DENSITY OR COLOR CODED BAND ARRAY, RELA-
    TIVE POWER
34  DENSITY OR COLOR CODED Z-TRANSFORMED
    BAND ARRAY
35  T-TEST CONDITION X vs. CONDITION Y
    (DENSITY CODED)
36  T-TEST PRESENT SAMPLE AGAINST NORM X
    (KEY STRIKE APPROPRIATE NORM KEY OR X)
                    Select A or B
A   actual values
B   Z-values
        TRAJECTORIES [either samples or sessions]
37  DELTA ABSOLUTE POWER, 8 CHANNEL, UP-
    DATING
38  DELTA RELATIVE POWER (%), 8 CHANNEL, UP-
    DATING
39  THETA ABSOLUTE POWER, 8 CHANNEL, UP-
    DATING
40  THETA RELATIVE POWER, 8 CHANNEL, UP-
    DATING
41  ALPHA ABSOLUTE POWER, 8 CHANNEL, UP-
    DATING
42  ALPHA RELATIVE POWER, 8 CHANNEL, UP-
    DATING
43  BETA ABSOLUTE POWER, 8 CHANNEL, UP-
    DATING
44  BETA RELATIVE POWER, 8 CHANNEL, UP-
    DATING
                        RAW DATA
45  SHOW CURRENT EEG SAMPLE + EKG, BP, RESP
46  SHOW SPIKES DETECTED IN CURRENT SAMPLE
47  SHOW EKG AT BOTTOM OF HEAD OR
    TRAJECTORY
```

For example, the user may select the following options, by operating the named keys, which are typical for an intraoperative procedure:

Key 8 (whole head); key 10 (1–100 Hz bandpass); key 13 (10.24 second epochlength); key 18 (previous minute, moving window); 24 (Gaussianity test for artifact rejection); 25 (store result on session disk); 33 (density coded band array, relative power); 38 (Delta relative power); 50 (head display).

This will give a moving window display, artifact-free, of Delta relative power on the whole 10/20 system, Z-transformed against the previous 60 seconds of artifact-free data.

As shown in FIG. 7, preferably the additional control panel 80, which may be based on a microcomputer keyboard having function keys, only has the function keys (22 function keys) and numerical keyboard 81 (10 keys) readily available to the user. The readily available portion is shown by the dashed line 82. The other portion of the keyboard is covered by a hinged cover 83 which has the options 1–36, set forth above.

What is claimed is:

1. An electroencephalographic (EEG) system including:

brain wave signal means to detect and amplify brain waves from the head of a patient, comprising a plurality of electrodes removably attached to a plurality of sectors of the patient's head to detect signals representing said brain waves, amplifiers connected to the electrodes, and analog/digital conversion means connected to the amplifiers to produce sets of digital data representing said brain waves from a selected plurality of sectors of the patient's head;

memory means to store selected reference normative data, said normative data being selected from the group of data for some prior state of the patient and data of population norms;

data analysis means connected to said brain wave signal means and said memory means to analyze the said brain wave signals on a statistical basis as compared to said reference normative data to produce a plurality of analysis samples; and display means connected to said data analyses means to visually display said analysis, characterized in that the display means comprises means to display said plurality of analysis samples as a plurality of rectangular stripes and means to modulate said stripes so that each of the stripes is modulated to represent the result of the said statistical analysis, the modulation being from the group of gray-scale code and color-code whose modulation is coded to the significance of the said statistical analysis; and means to form said stripes into a pile of said stripes, said pile having opposite ends with an oldest-in-time stripe at one end, and a youngest-in-time stripe at the opposite end, said pile forming a moving window display in which the oldest-in-time stripe at one end of the pile is removed and replaced by a new youngest-in-time stripe at the opposite end of the pile.

2. An EEG system as in claim 1 wherein the display means includes a head diagram having display sectors representing a plurality of head sectors, said stacks form a plurality of said moving window displays, each one of the said moving window displays being shown in each display sector to provide information concerning the brain waves occurring in the corresponding region of the patient's head represented by the display sector.

3. An EEG system as in claim 2 wherein the electrodes consist of four pairs of electrodes to detect brain waves in eight head sectors.

4. An EEG system as in claim 1 wherein said data analysis means includes means to perform a spectral analysis of a selected frequency band of data.

5. An EEG system as in claim 4 wherein said spectral analysis means is a Fourier Transform means.

6. An EEG system as in claim 1 wherein the display means includes means to display a border around said stack, and means to flash the border as an alarm for conditions which are abnormal compared to said reference normative data.

7. An electroencephalograph (EEG) system including:

brain wave signal means to detect and amplify the waves from the head of a patient comprising a plurality of electrodes adapted to be connected to the patient's head to detect signals representing said brain waves, amplifiers connected to the electrodes, and analog/digital conversion means connected to the amplifiers to produce sets of digital data representing said brain waves from a plurality of sectors of the head;

data analysis means connected to said brain wave signal means to analyze the said brain wave signals on a statistical basis in comparison to a set of normative data;

display means connected to said data analysis means to visually display the results of said analysis; the data being displayed in the form of a topological map with each area of the map corresponding in location to a sector of the patient's head;

characterized in that:

the said areas are blocks, each of which blocks having a plurality of sub-areas which are arranged in sub-areas formed in rows and columns, with rows representing sequential analyses and columns representing different measures, and with gaps between the blocks;

each of the sub-areas of the blocks is color-coded so that its color is directly related to the result of said statistical analysis of the corresponding head sector within or across measures.

8. An EEG system as in claim 7 wherein the display means includes means to display a border about each of the said blocks and means to flash the border on-off as a warning signal for a condition which is abnormal compared to said reference normative data.

9. An EEG system as in claim 7 and further characterized in that a plurality of color-coded row bars extend between the blocks of each row, and the system includes means to control the color of the row bars so that their color is a display of the results of statistical analysis on the relationships between the head sectors corresponding to the blocks of said rows.

10. An EEG system as in claim 7 and further characterized in that a plurality of color-coded column bars extend between the blocks of each column, and the system includes means to control the color of the column bars so that their color is a display of the results of statistical analysis on the relationships between the head areas corresponding to the blocks of said columns.

11. An electroencephalograph (EEG) system including:

brain wave signal means to detect and amplify the brain waves from the head of a patient comprising a plurality of electrodes adapted to be connected to the patient's head to detect signals representing the said brain waves, amplifiers connected to the electrodes, and analog/digital conversion means connected to the amplifiers to produce sets of digital data corresponding to the patient's brain waves from a plurality of sectors of the patient's head;

memory means to store reference normative data selected from the group of some prior state of the patient and population norms;

data analysis means connected to said brain wave signal means and to said memory means to analyze the said brain wave signals on a statistical basis on comparison to said normative data;

display means including a CRT screen to visually display said analysis; wherein the data is displayed in the form of a topological map in which each area of the map corresponds in location to a sector of the patient's head;

characterized in that:

the said areas on the CRT screen are arranged in rows and columns, each of the areas consisting of a separated shape with gaps between said shapes and each shape representing the EEG feature derived from the group of the complete energy spectrum of brain waves, the absolute or relative (%) power from one or more frequency bands, coherence as between one or more frequency bands, and asymmetry as between frequency bands; and the system includes:

means to color-code each of the shapes so that the color of said shape is directly related to the result of said statistical analysis of the EEG factor at the corresponding head sector or the relations between two sectors and means to display on said CRT screen a plurality of color-coded bars connecting the said areas and means to control the color of the said bars to display relationships between the said areas.

12. An EEG system as in claim 11 wherein each of the areas consists of sub-areas comprising a plurality of geometric shapes arranged in rows and columns with the rows indicating the said analysis results over a tandem series of time periods, and the columns representing different extracted features and the shape being selected from the group of dots, bar and line segments.

13. An EEG system as in claim 11 and further including means to display a border about each of the said areas, and means to flash the border on-off as a warning signal.

14. An EEG system as in claim 11 and further including means to selectively display the areas or bars separately or superimposed on each other on said display.

15. An electroencephalograph (EEG) system including:

brain wave signal means to detect and amplify the brain waves from the head of a patient comprising a plurality of electrodes, each electrode being adapted to be connected to a sector of the patient's head to detect signals representing the patient's brain waves at the sector to which it is connected, amplifiers connected to the electrodes, an analog/digital conversion means connected to the amplifiers to produce sets of digital data representing the patient's brain waves from the said head sectors;

data analysis means connected to said conversion means to analyze the digital brain wave signals on a statistical basis in comparison to a set of stored normative data to produce a head sector relationship analysis which is a statistical analysis of the coherence relationship between the brain waves from each head sector and the brain waves from every other head sector, in a selected frequency band;

display means connected to said data analysis means to visually display the results of the said head sector coherence analysis; wherein the said analysis is displayed in the form of a topological map in which each area of the map corresponds in location to a patient head sector;

wherein:

the said map areas at least twenty map areas are arranged such that each of the map areas is itself arranged as an array of dots representing the position of each electrode, with one dot representing a head sector and the other dots representing the said statistical analysis of the coherence between the sector represented by the said one dot and the other head sectors, in any selected frequency band, and the system further including:

means to color-code each of the dots so that its color corresponds to the result of said statistical coherence analysis.

16. An EEG system as in claim 15 wherein each of the dots is a rectangle.

17. An EEG system as in claim 15 wherein the display is of a plurality of the said maps, each of said maps indicating the relationship between the head sectors.

18. An EEG system as in claim 17 wherein the measures are selected from the group consisting of absolute power and relative power in at least four frequency bands.

19. An EEG system as in claim 17 wherein the system includes computer means to subject the power data to Z-transformation based upon computer stored norms.

20. An EEG system as in claim 15 wherein said data analysis means includes a spectral analysis means to analyze data selected from the group of the full spectrum of the waves, at least four absolute power frequency bands, at least four relative power frequency bands, and frequency amplitude spectrum coherence as between at least four frequency bands.

* * * * *